US012758796B2

(12) United States Patent
Seco et al.

(10) Patent No.: US 12,758,796 B2
(45) Date of Patent: Oct. 13, 2026

(54) APPARATUS FOR RADIOTHERAPY AND METHOD OF OPERATING AN APPARATUS FOR RADIOTHERAPY

(71) Applicant: DEUTSCHES KREBSFORSCHUNGSZENTRUM STIFTUNG DES OFFENTLICHEN RECHTS, Heidelberg (DE)

(72) Inventors: Joao Seco, Heidelberg (DE); Joao Pedro Oliveira Lourenco, Heidelberg (DE); Filipa Baltazar, Heidelberg (DE)

(73) Assignee: DEUTSCHES KREBSFORSCHUNGSZENTRUM STIFTUNG DES OFFENTLICHEN RECHTS, Heidelberg (DE)

( * ) Notice: Subject to any disclaimer, the term of this patent is extended or adjusted under 35 U.S.C. 154(b) by 151 days.

(21) Appl. No.: 18/833,169

(22) PCT Filed: Jan. 25, 2023

(86) PCT No.: PCT/EP2023/051842
§ 371 (c)(1),
(2) Date: Jul. 25, 2024

(87) PCT Pub. No.: WO2023/144234
PCT Pub. Date: Aug. 3, 2023

(65) Prior Publication Data
US 2025/0108234 A1 Apr. 3, 2025

(30) Foreign Application Priority Data
Jan. 27, 2022 (EP) .................................... 22153599

(51) Int. Cl.
*A61N 5/10* (2006.01)

(52) U.S. Cl.
CPC ......... *A61N 5/1048* (2013.01); *A61N 5/1031* (2013.01); *A61N 5/1045* (2013.01);
(Continued)

(58) Field of Classification Search
None
See application file for complete search history.

(56) References Cited

FOREIGN PATENT DOCUMENTS

| | | | | |
|---|---|---|---|---|
| EP | 3881895 A1 | | 9/2021 | |
| EP | 3928833 A1 | * | 12/2021 | ........... A61N 5/1042 |

(Continued)

OTHER PUBLICATIONS

Mazal A. et al., "Biological and Mechanical Synergies to Deal With Proton Therapy Pitfalls: Minibeams, FLASH, Arcs, and Gantryless Rooms", Frontiers in Oncology 10:613669 (Jan. 2021).

(Continued)

*Primary Examiner* — Hoon K Song
(74) *Attorney, Agent, or Firm* — Scully, Scott, Murphy & Presser, P.C.

(57) ABSTRACT

The present disclosure provides an apparatus for radiotherapy. The apparatus includes at least one first radiation source configured to provide one or more ultra-high dose rate charged particle beams; at least one second radiation source configured to provide one or more intensity-modulated beams; and a controller. The controller is configured to control the at least one first radiation source to generate the one or more ultra-high dose rate charged particle beams and control the at least one second radiation source to generate the one or more intensity-modulated beams such that the one or more ultra-high dose rate charged particle beams and the one or more intensity-modulated beams provide a substantially uniform total dose distribution across the target region.

14 Claims, 12 Drawing Sheets

(52) U.S. Cl.
CPC .... *A61N 5/1084* (2013.01); *A61N 2005/1074* (2013.01); *A61N 2005/1087* (2013.01)

(56) References Cited

FOREIGN PATENT DOCUMENTS

| | | | | | |
|---|---|---|---|---|---|
| EP | 3881895 | B1 | * | 7/2023 | ........... A61N 5/1031 |
| WO | 2021061666 | A1 | | 4/2021 | |

OTHER PUBLICATIONS

International Search Report dated Apr. 6, 2023 issued in PCT/EP2023/051842.

Written Opinion dated Apr. 6, 2023 issued in PCT/EP2023/051842.

* cited by examiner (a)

(b)

APPARATUS FOR RADIOTHERAPY AND METHOD OF OPERATING AN APPARATUS FOR RADIOTHERAPY

FIELD

Embodiments of the present disclosure relate to an apparatus for radiotherapy, a method of operating an apparatus for radiotherapy, and a computer-readable storage medium for executing the method. Embodiments of the present disclosure relate more particularly to multi-beam proton therapy in cancer treatment.

BACKGROUND

According to the World Health Organization, cancer is the second leading cause of death globally, right after cardiovascular diseases. As a result, substantial effort has been put into improving treatment options. Radiotherapy has been used as a tool for cancer treatment for more than one hundred years. Radiotherapy targets a tumor with ionizing radiation, which damages and eventually kills the tumor cells.

In general, two different types of radiotherapy can be distinguished: internal radiotherapy, in which the radiation source is a radioactive material located inside the body, and external radiotherapy, in which the radiation source is provided by a radiation system located outside the body.

Various radiation sources can be used in external radiotherapy. For example, X-rays can be used as a radiation source, but charged particles such as protons and electrons can also be considered for radiotherapy. Charged particles interact differently with tissue than photons and produce more localized dose deposition profiles in tissue depending on the incident energy. Thus, by modulating the energy of the charged particle beam, tumors in different positions can be targeted.

Even though the efficacy of external radiotherapy is based on the damaging effect on the cancer cells caused, for example, by charged particles, the damaging effect cannot be limited to the cancer cells. Thus, external radiotherapy can also have harmful effects on surrounding healthy cells, resulting in radiation toxicity. This results in a natural paradigm: on the one hand, a sufficient dose is needed to fight the tumor; on the other hand, too high a radiation dose can have serious toxic effects on the patient.

In view of the above, new apparatuses for radiotherapy, methods of operating an apparatus for radiotherapy, and computer-readable storage media for executing the methods, that overcome at least some of the problems in the art are beneficial.

SUMMARY

In light of the above, an apparatus for radiotherapy, a method of operating an apparatus for radiotherapy, and a computer-readable storage medium for executing the method are provided.

It is an object of the present disclosure to improve an efficiency of an apparatus for external radiotherapy. It is another object of the present disclosure to minimize toxic effects on a patient.

The objects are solved by the features of the independent claims. Preferred embodiments are defined in the dependent claims.

According to an independent aspect of the present disclosure, an apparatus for radiotherapy, in particular FLASH radiotherapy, is provided. The apparatus includes at least one first radiation source configured to provide one or more first beams; at least one second radiation source configured to provide one or more second beams; and a controller configured to control the at least one first radiation source and the at least one second radiation source.

According to some embodiments, which can be combined with other embodiments described herein, the one or more first beams and the one or more second beams are generated sequentially. For example, the one or more first beams and the one or more second beams can be pulsed beams that are generated and emitted intermittently.

The one or more first beams can include, or be, one or more charged particle beams. In particular, the one or more charged particle beams can include, or be, one or more ultra-high dose (rate) charged particle beams.

Preferably, the one or more charged particle beams are pulsed beams.

According to some embodiments, which can be combined with other embodiments described herein, the one or more ultra-high dose rate charged particle beams are one or more FLASH beams, i.e., beams for FLASH radiotherapy (FLASH-RT).

According to some embodiments, which can be combined with other embodiments described herein, the one or more ultra-high dose rate charged particle beams are modulated to provide the FLASH effect at one or more volumes of interest, such as Organs At Risk (OAR). The constraints for the FLASH effect can include a minimum dose of 8, 10 or 12 Gy (in particular 8 or 10 Gy/pulse) in the one or more volumes of interest and a minimum dose rate of 30, 40 or 50 Gy/s in the one or more volumes of interest.

Preferably, the one or more volumes of interest, such as one or more OARs, are spatially separated from and/or adjacent to a target region, such as a Planning Target Volume (PTV) which includes a tumor to be treated.

According to some embodiments, which can be combined with other embodiments described herein, the controller is configured to control the at least one first radiation source such that each ultra-high dose rate charged particle beam passes through a respective volume of interest.

Preferably, a number of ultra-high dose rate charged particle beams and a number of volumes of interest are the same.

Preferably, the controller is further configured to control the at least one second radiation source so that that the one or more second beams, such as one or more intensity-modulated (e.g., IMPT, IMRT or VMAT) beams, do not pass through any of the volumes of interest.

According to some embodiments, which can be combined with other embodiments described herein, the one or more charged particle beams are selected from the group including, or consisting of, proton beams, electron beams and ion beams.

According to some embodiments, which can be combined with other embodiments described herein, the one or more first beams, in particular the one or more ultra-high dose rate charged particle beams, are Single Field Uniform Dose (SFUD) beams.

According to some embodiments, which can be combined with other embodiments described herein, the one or more second beams can include, or be, one or more intensity-modulated beams.

According to some embodiments, which can be combined with other embodiments described herein, the one or more second beams, in particular the one or more intensity-modulated beams, are selected from the group including, or consisting of, photon beams (e.g., X-ray), proton beams, electron beams and ion beams.

Preferably, the one or more second beams, in particular the one or more intensity-modulated beams are Intensity Modulated Proton Therapy (IMPT) beams, Intensity Modulated Radiotherapy (IMRT) beams, or Volumetric Intensity Modulated Arc Therapy (VMAT) beams.

According to some embodiments, which can be combined with other embodiments described herein, the controller is configured to control the at least one first radiation source to generate the one or more ultra-high dose rate charged particle beams and control the at least one second radiation source to generate the one or more intensity-modulated beams such that the one or more ultra-high dose rate charged particle beams and the one or more intensity-modulated beams provide a substantially uniform total dose distribution across the target region.

Preferably, the controller is further configured to control the at least one first radiation source to generate the one or more ultra-high dose rate charged particle beams and control the at least one second radiation source to generate the one or more intensity-modulated beams such that a first dose distribution of the one or more ultra-high dose rate charged particle beams and a second dose distribution of the one or more intensity-modulated beams combine (or add up) in the target region to provide the substantially uniform total dose distribution across the target region, e.g., across substantially the entire target region (TV).

According to some embodiments, which can be combined with other embodiments described herein, the controller is configured to control the at least one first radiation source to generate the one or more ultra-high dose rate charged particle beams such that each ultra-high dose rate charged particle beam of the one or more ultra-high dose rate charged particle beams provides a substantially uniform first dose distribution in a corresponding first region of a target region; and control the at least one second radiation source to generate the one or more intensity-modulated beams such that the one or more intensity-modulated beams provide a substantially uniform second dose distribution in a second region of the target region different from the first region.

Therefore, the one or more intensity-modulated beams contribute to the complete homogeneous coverage of the target region and prevent the formation of cold spots. In particular, the one or more intensity-modulated beams can "stitch" the first (e.g., FLASH) regions or "fill in" the region(s) of the target volume not covered by the ultra-high dose rate charged particle beam(s) (e.g., FLASH beams). Consequently, the one or more ultra-high dose rate charged particle beams and the one or more intensity-modulated beams are interdependent, i.e., the one or more ultra-high dose rate charged particle beams and the one or more intensity-modulated beams, in particular the doses and dose rates provided by them, cannot be considered independently from each other.

According to some embodiments, which can be combined with other embodiments described herein, a dose value of the substantially uniform first dose distribution and a dose value of the substantially uniform second dose distribution are substantially the same.

According to some embodiments, which can be combined with other embodiments described herein, the first region(s) and the second region do not overlap.

According to some embodiments, which can be combined with other embodiments described herein, the target region includes, or consists of, the first region(s) and the second region.

According to some embodiments, which can be combined with other embodiments described herein, at least one interface region is provided between the first region(s) and the second region.

According to some embodiments, which can be combined with other embodiments described herein, the target region includes, or consists of, the first region, the second region and at least one interface region between the first region and the second region.

According to some embodiments, which can be combined with other embodiments described herein, the controller is further configured to control the at least one first radiation source and the at least one second radiation source to provide a substantially uniform total dose distribution across the first region(s) and the second region and optionally the at least one interface region.

According to further embodiments, which can be combined with other embodiments described herein, the controller is configured to control the at least one first radiation source to generate the one or more ultra-high dose rate charged particle beams and control the at least one second radiation source to generate the one or more intensity-modulated beams such that dose distributions of the one or more ultra-high dose rate charged particle beams and the one or more intensity-modulated beams spatially overlap and add up in the at least one interface region to provide the substantially uniform total dose distribution across the at least one interface region.

Preferably, the dose distributions of the one or more ultra-high dose rate charged particle beams and the one or more intensity-modulated beams in the at least one interface region are non-uniform. For example, vertical dose profiles of the one or more ultra-high dose rate charged particle beams and the one or more intensity-modulated beams in the at least one interface region can each have a gradient. In some embodiments, the vertical dose profiles have opposite slopes, such as inclining and declining, respectively.

According to further embodiments, which can be combined with other embodiments described herein, the controller is configured to control the at least one first radiation source to generate the one or more ultra-high dose rate charged particle beams and control the at least one second radiation source to generate the one or more intensity-modulated beams such that dose distributions of the one or more ultra-high dose rate charged particle beams and the one or more intensity-modulated beams spatially overlap and/or add up in the target region to provide the substantially uniform total dose distribution across the target region.

Therefore, the one or more ultra-high dose rate charged particle beams and the one or more intensity-modulated beams contribute to the complete homogeneous coverage of the target region and prevent the formation of cold spots. Consequently, the one or more ultra-high dose rate charged particle beams and the one or more intensity-modulated beams are interdependent, i.e., the one or more ultra-high dose rate charged particle beams and the one or more intensity-modulated beams, in particular the doses and dose rates provided by them, cannot be considered independently from each other.

Preferably, the controller is further configured to control the at least one first radiation source to generate the one or more ultra-high dose rate charged particle beams such that the dose distribution of the one or more ultra-high dose rate charged particle beams across the target region is non-uniform; and control the at least one second radiation source to generate the one or more intensity-modulated beams such that the dose distribution of the one or more intensity-modulated beams across the target region is non-uniform.

For example, vertical dose profiles of the one or more ultra-high dose rate charged particle beams and the one or more intensity-modulated beams in the at least one interface region can each have a gradient to provide the non-uniform dose distributions across the target region. In some embodiments, the vertical dose profiles have opposite slopes, such as inclining and declining, respectively.

Preferably, the non-uniform dose distributions of the one or more ultra-high dose rate charged particle beams and the one or more intensity-modulated beams spatially overlap and/or add up in the target region to provide the substantially uniform total dose distribution across the target region.

Since the beams have non-uniform dose distributions across the target region, i.e., a wide range, the irradiation is robust against movement of the target. In particular, movement of the target within a considerable range does not affect the uniformity of the total dose distribution across the target region.

In the above example, the dose distributions of the one or more ultra-high dose rate charged particle beams and the one or more intensity-modulated beams in the target region are non-uniform. For example, vertical dose profiles of the one or more ultra-high dose rate charged particle beams and the one or more intensity-modulated beams in the at least one interface region can each have a gradient. In some embodiments, the vertical dose profiles have opposite slopes, such as inclining and declining, respectively.

According to some embodiments, which can be combined with other embodiments described herein, the controller is further configured to control the at least one first radiation source and the at least one second radiation source to provide a substantially uniform total dose distribution across substantially the entire target region.

Preferably, the controller is further configured to control the at least one first radiation source such that the one or more intensity-modulated beams fill in doses of regions of the target volume not covered by the one or more ultra-high dose rate charged particle beams to provide the substantially uniform total dose distribution across substantially the entire target region.

According to the embodiments of the present disclosure, "substantially uniform" is understood to refer to the dose distribution in a target or a particular target region in such a way that a deviation from an exactly constant dose distribution is possible. That is, "substantially uniform dose distribution" relates to a substantially uniform dose distribution in the target or target region, with a deviation of, for example, up to 5%, 10% or even 15% from an exactly constant dose distribution (e.g., a reference dose, prescribed dose, or an average/mean value of the dose deposited in the target or target region) still considered a "substantially uniform dose distribution". This deviation can exist, for example, due to natural changes in the patient's anatomy and/or machine-related uncertainties or tolerances. However, the dose distribution in the target or specific target region is considered to be substantially uniform.

According to some embodiments, which can be combined with other embodiments described herein, the controller is further configured to sequentially determine a dose and a dose rate for the target volume.

Preferably, the controller is configured to determine a configuration (e.g., fluence and/or intensity) of the one or more ultra-high dose rate charged particle beams based on one or more dose constraints; determine a configuration (e.g., fluence and/or intensity) of the one or more intensity-modulated beams based on a dose deposited in the target volume by the one or more ultra-high dose rate charged particle beams; and optimize the configuration (e.g., fluence and/or intensity) of the one or more ultra-high dose rate charged particle beams based on one or more dose rate constraints.

Preferably, the one or more dose constraints include one or more FLASH constraints, such as a minimum dose to be deposited in one or more volumes of interest (e.g., OARs). For example, the minimum dose can be 8 Gy or more, 10 Gy or more, or 12 Gy or more.

Preferably, the one or more dose rate constraints include one or more FLASH dose rate constraints, such as a minimum dose rate to be provided in one or more volumes of interest (e.g., OARs). For example, the minimum dose rate can be 30 Gy/s or more, 40 Gy/s or more, or 50 Gy/s or more.

In further embodiments, which can be combined with other embodiments described herein, the controller is configured to simultaneously determine a dose and a dose rate for the target volume.

Preferably, the controller is configured to determine a first influence matrix for the one or more ultra-high dose rate charged particle beams and a second influence matrix for the one or more intensity-modulated beams; combine the first influence matrix and the second influence matrix to obtain a combined matrix; and optimize the combined matrix to determine a configuration (e.g., fluence and/or intensity) of the one or more ultra-high dose rate charged particle beams and a configuration (e.g., fluence and/or intensity) of the one or more intensity-modulated beams.

Preferably, the controller is configured to perform the optimizing considering one or more dose constraint and one or more dose rate constraints in one or more volumes of interest (e.g., OARs).

Preferably, the one or more dose constraints include one or more FLASH constraints, such as a minimum dose to be deposited in one or more volumes of interest (e.g., OARs). For example, the minimum dose can be 8 Gy or more, 10 Gy or more, or 12 Gy or more.

Preferably, the one or more dose rate constraints include one or more FLASH dose rate constraints, such as a minimum dose rate to be provided in one or more volumes of interest (e.g., OARs). For example, the minimum dose rate can be 30 Gy/s or more, 40 Gy/s or more, or 50 Gy/s or more.

According to another independent aspect of the present disclosure, a method of operating an apparatus for radiotherapy is provided. The method includes controlling at least one first radiation source to irradiate a target region with one or more ultra-high dose rate charged particle beams such that each ultra-high dose rate charged particle beam of the one or more ultra-high dose rate charged particle beams provides a substantially uniform first dose distribution in a corresponding first region of the target region; and controlling at least one second radiation source to irradiate the target region with one or more intensity-modulated beams such that the one or more intensity-modulated beams provide a substantially uniform second dose distribution in a second region of the target region different from the first region.

According to some embodiments, which can be combined with other embodiments described herein, the one or more intensity-modulated beams fill in doses of regions of the target volume not covered by the one or more ultra-high dose rate charged particle beams to provide a substantially uniform total dose distribution across the target region.

According to some embodiments, which can be combined with other embodiments described herein, the one or more ultra-high dose rate charged particle beams and the one or more intensity-modulated beams are pulsed beams, and the target region is irradiated sequentially with the one or more ultra-high dose rate charged particle beams and the one or more intensity-modulated beams.

According to some embodiments, which can be combined with other embodiments described herein, the method further includes sequentially determining a dose and a dose rate for the target volume.

Preferably, sequentially determining a dose and a dose rate for the target volume includes determining a configuration (e.g., fluence and/or intensity) of the one or more ultra-high dose rate charged particle beams based on one or more dose constraints; determining a configuration (e.g., fluence and/or intensity) of the one or more intensity-modulated beams based on a dose deposited in the target volume by the one or more ultra-high dose rate charged particle beams; and optimizing the configuration (e.g., fluence and/or intensity) of the one or more ultra-high dose rate charged particle beams based on one or more dose rate constraints.

Preferably, the one or more dose constraints include one or more FLASH constraints, such as a minimum dose to be deposited in one or more volumes of interest (e.g., OARs). For example, the minimum dose can be 8 Gy or more, 10 Gy or more, or 12 Gy or more.

Preferably, the one or more dose rate constraints include one or more FLASH dose rate constraints, such as a minimum dose rate to be provided in one or more volumes of interest (e.g., OARs). For example, the minimum dose can be 30 Gy/s or more, 40 Gy/s or more, or 50 Gy/s or more.

In further embodiments, which can be combined with other embodiments described herein, the method includes simultaneously determining a dose and a dose rate for the target volume.

Preferably, simultaneously determining a dose and a dose rate for the target volume includes determining a first influence matrix for the one or more ultra-high dose rate charged particle beams and a second influence matrix for the one or more intensity-modulated beams; combining the first influence matrix and the second influence matrix to obtain a combined matrix; and optimizing the combined matrix to determine a configuration (e.g., fluence and/or intensity) of the one or more ultra-high dose rate charged particle beams and a configuration (e.g., fluence and/or intensity) of the one or more intensity-modulated beams.

Preferably, the optimizing is performed considering one or more dose constraints and one or more dose rate constraints in one or more volumes of interest (e.g., OARs).

Preferably, the one or more dose constraints include one or more FLASH constraints, such as a minimum dose to be deposited in one or more volumes of interest (e.g., OARs). For example, the minimum dose can be 8 Gy or more, 10 Gy or more, or 12 Gy or more.

Preferably, the one or more dose rate constraints include one or more FLASH dose rate constraints, such as a minimum dose rate to be provided in one or more volumes of interest (e.g., OARs). For example, the minimum dose can be 30 Gy/s or more, 40 Gy/s or more, or 50 Gy/s or more.

Embodiments are also directed at apparatus aspects for carrying out the disclosed method and include method aspects for performing each described apparatus aspect. These method aspects can be performed by way of hardware components, a computer programmed by appropriate software, by any combination of the two or in any other manner. Furthermore, embodiments according to the disclosure are also directed at methods of operating the described apparatus. The disclosure includes method aspects for carrying out every function of the apparatus.

According to another independent aspect of the present disclosure, a machine-readable storage medium is provided. The machine-readable storage medium includes instructions executable by one or more processors to implement the method of operating an apparatus for radiotherapy of the embodiments of the present disclosure.

According to another independent aspect of the present disclosure, a machine-readable storage medium is provided. The machine-readable storage medium includes instructions stored, that, when executed, cause one or more processors to perform control of at least one first radiation source to irradiate a target region with one or more ultra-high dose rate charged particle beams; and control of at least one second radiation source to irradiate the target region with one or more intensity-modulated beams.

Preferably, control of the at least one first radiation source and the at least one second radiation source is performed such that the one or more ultra-high dose rate charged particle beams and the one or more intensity-modulated beams provide a substantially uniform total dose distribution across the target region.

The (e.g., non-transitory) machine readable storage medium can include, for example, optical media such as CD-ROMs and digital video disks (DVDs), and semiconductor memory devices such as Electrically Programmable Read-Only Memory (EPROM), and Electrically Erasable Programmable Read-Only Memory (EEPROM). The machine-readable medium can be used to tangibly retain computer program instructions or code organized into one or more modules and written in any desired computer programming language. When executed by, for example, one or more processors such computer program code can implement one or more of the methods described herein.

According to another independent aspect of the present disclosure, an apparatus for radiotherapy is provided. The apparatus includes one or more processors; and a memory (e.g., the above machine-readable medium) coupled to the one or more processors and comprising instructions executable by the one or more processors to implement the method of operating an apparatus for radiotherapy of the embodiments of the present disclosure.

BRIEF DESCRIPTION OF THE DRAWINGS

So that the manner in which the above recited features of the present disclosure can be understood in detail, a more particular description of the disclosure, briefly summarized above, can be had by reference to embodiments. The accompanying drawings relate to embodiments of the disclosure and are described in the following.

DETAILED DESCRIPTION OF EMBODIMENTS

Reference will now be made in detail to the various embodiments of the disclosure, one or more examples of which are illustrated in the figures. Within the following description of the drawings, the same reference numbers refer to same components. Generally, only the differences with respect to individual embodiments are described. Each example is provided by way of explanation of the disclosure and is not meant as a limitation of the disclosure. Further, features illustrated or described as part of one embodiment can be used on or in conjunction with other embodiments to yield yet a further embodiment. It is intended that the description includes such modifications and variations.

Figure 1:
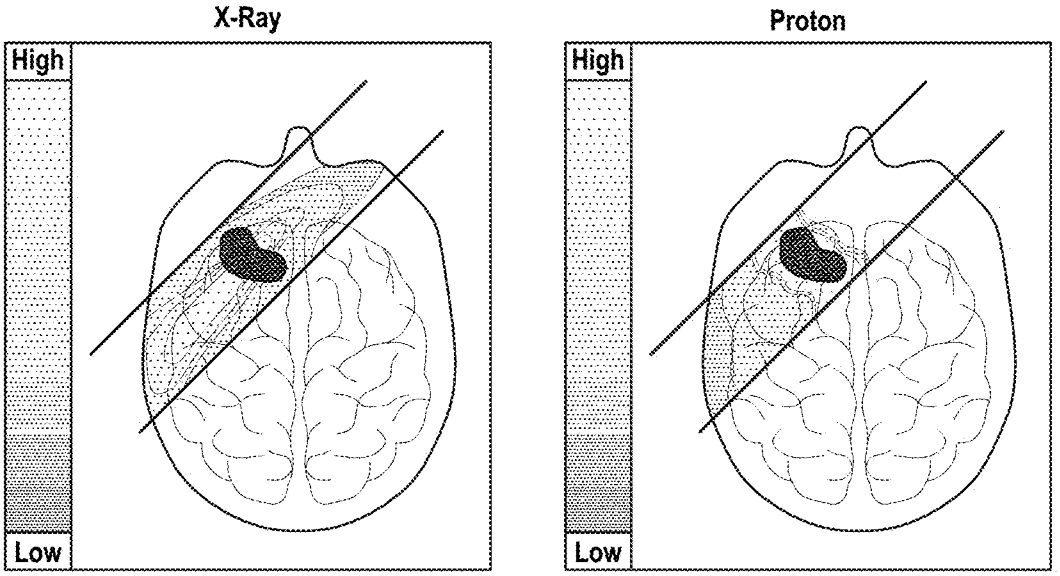
FIG. 1 shows a dose distribution for X-rays on the left and a dose distribution for protons on the right.

Radiotherapy has been used as a tool for cancer treatment for more than one hundred years. Radiotherapy targets a tumor with ionizing radiation, which damages and eventually kills the tumor cells. Various radiation sources can be used in external radiotherapy. For example, X-rays can be used as a radiation source, but charged particles such as protons and electrons can also be considered for radiotherapy. Charged particles interact differently with tissue than photons and produce more localized dose deposition profiles in tissue depending on the incident energy. This is illustrated in FIG. 1, which shows a dose distribution for X-rays on the left and a dose distribution for protons on the right. Thus, by modulating the energy of the charged particle beam, tumors in different positions can be targeted.

The following description uses the concept of dose, which is defined as the energy (Joule) delivered per unit mass (kilogram) and is expressed in units of Gray (Gy). The Gray is used as a unit of the radiation quantity absorbed dose that measures the energy deposited by ionizing radiation in a unit mass of matter being irradiated, and is used for measuring the delivered dose of ionizing radiation radiotherapy. Often, treatments are based on a total dose that should be delivered to the tumor site, possibly specifying a maximum dose that can be delivered to surrounding healthy regions.

Figure 2:
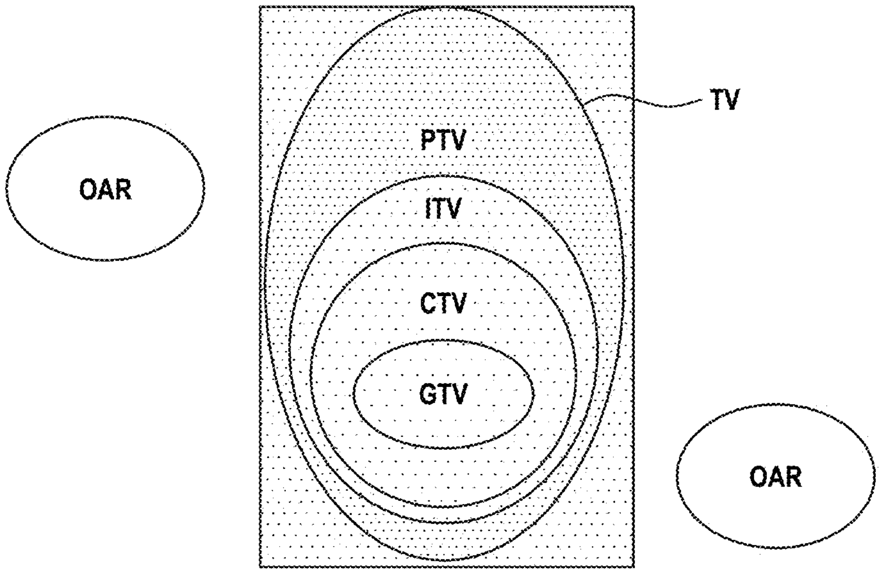
FIG. 2 shows a target volume used in radiotherapy.

FIG. 2 shows a target volume used in radiotherapy. For example, once an image of the patient's anatomy is available, the structures relevant for treatment, in particular volumes of interest such as Organs At Risk (OAR), are defined.

A volume of interest can include, or be, a target volume TV, which is usually described in terms of four main volumes: The Gross Tumor Volume (GTV), the Clinical Target Volume (CTV), the Internal Tumor Volume (ITV), and the Planning Target Volume (PTV).

The Gross Tumor Volume (GTV) indicates the volume that is identified by a physician by looking at an image of the volume or an algorithm analyzing, for example, CT data.

The Clinical Target Volume (CTV) consists of the GTV with an extra margin around. This margin is defined based on the probability level that the surrounding tissue is still considered malignant.

The Internal Tumor Volume (ITV) consists of the CTV and an additional margin that accounts for physiological variations of the CTV (e.g., in size and shape).

The Planning Target Volume (PTV) is the key volume in radiotherapy planning. The additional margin around the CTV that defines the PTV accounts for uncertainties in dose delivery. That is, these margins are taken into account to ensure that the correct dose is delivered to the CTV, regardless of possible variations to which radiotherapy is highly susceptible, whether due to natural changes in the patient's anatomy or machine-related uncertainties.

In addition to the target volume TV, other volumes of interest can be identified, such as at least one Organ At Risk (OAR). These volumes can contain healthy organs that should also be considered in treatment planning due to their sensitivity to radiation. In these regions, the radiation dose should be minimal or have only a certain value. An additional margin around the OAR can also be defined to account for uncertainties during treatment.

When determining the volumes of interest, planning is done so that there is a constant balance between achieving the desired dose at the target volume (TV=PTV) and minimizing the dose to which the specified OAR(s) is/are exposed.

External Radiotherapy

In general, two types of radiation can be used in external radiotherapy: electromagnetic radiation (e.g., X-rays) and charged particles (e.g., protons, ions, or electrons). Charged particles interact with tissue differently than electromagnetic radiation. As can be seen in FIG. 1, while photons exhibit a dose deposition profile that changes quite slowly in tissue, the dose deposition profile of protons exhibits a sudden increase in dose deposition at a particular depth point or depth region, resulting in a maximum deposited dose at that depth point (single Bragg-Peak) or depth region (Spread-Out Bragg peak, SOBP). Consequently, the involvement of a different radiation directly leads to a different clinical outcome.

FLASH Radiotherapy

FLASH radiotherapy (FLASH-RT) is a sub-type of external radiotherapy that uses ultra-high dose rates for the charged particle beams. FLASH radiotherapy has been associated with a reduction in radiation-induced toxicity effects while maintaining the same response for tumor tissue.

FLASH-RT uses ultrafast irradiation with dose rates that are several orders of magnitude higher than the dose rates used in conventional radiotherapy (e.g., 35-100 Gy/s compared to 1-4 Gy/min). Thus, with FLASH-RT, there are no longer any problems with organ motion because the tissue is irradiated for only short periods of time, usually less than 0.1 seconds. In addition, several studies have shown that the high dose rates allow for the reduction of toxicity directly induced by radiation to normal tissue while maintaining an equally effective response to tumor tissue. This is the so-called "FLASH effect".

One of the best known hypotheses to explain the FLASH effect is based on oxygen depletion. Oxygen is a molecule that is considered a radiation sensitizer: due to its large electron affinity, oxygen contributes to the conversion of radiation-induced damage, which can still be repaired by cellular mechanisms, into permanent damage to DNA. According to the oxygen depletion hypothesis, when tissue is irradiated with very high doses, as in FLASH-RT, oxygen is removed from the cell much faster than it is returned to the cell by diffusion processes in healthy tissue, creating a hypoxic situation in the cell. As a result, the radiation sensitizer effect of oxygen is absent. In addition, the lack of oxygen in the cell leads to a reduction in the formation of reactive oxygen species in the irradiation process and thus attenuates its potential toxic effect on the cell.

However, the oxygen depletion hypothesis might not be the only explanation for the FLASH effect, and further research is currently underway to determine the mechanisms responsible for, or contributing to, the FLASH effect.

FLASH-RT uses charged particle beams to irradiate tumors. The charged particles can be protons, electrons, or ions.

The type of charged particles used in radiotherapy can be selected based on various factors, such as the type of tumor, the location of the tumor in the patient's body, the accessibility of the techniques, and the like. For example, the energy range of electron beams commonly used in radiotherapy only allows irradiation of superficial regions. Protons or ions, on the other hand, can be used to treat tumors that lie deeper in the patient's body.

The charged particles can be supplied by a particle accelerator that uses electromagnetic fields to bring the charged particles to desired energies and maintain the charged particles in well-defined charged particle beams. For example, linear accelerators, cyclotrons, or synchrotrons can be used to generate proton beams and/or ion beams for FLASH-RT.

In a preferred embodiment, the particle accelerator is configured to generate a Spread-Out Bragg peak, SOBP, FLASH dose. The SOBP FLASH dose can be created by varying the energy of the charged particle beam, using different energies with appropriate weighting to produce a flat, even SOBP.

Charged Particle Delivery Techniques

The shape of the charged particle beam can be modulated before the tumor is irradiated. Beam shaping can be accomplished by a suitable means such as a "nozzle" located at the exit of a radiation source. There are two main charged particle delivery techniques that can be used: Passive Scattering (PS) and Pencil Beam Scanning (PBS), or simply Pencil Beam.

In Passive Scattering (PS), at least one scattering device can be positioned such that the charged particle beam is laterally broadened. In addition, a range modulator device configured for longitudinal modulation of the charged particle beam can be positioned after the at least one scattering device.

Pencil Beam Scanning (PBS) uses magnetic fields to deflect the charged particle beam using the Lorenz force to scan the charged particle beam over a specific area. PBS allows more flexible beam shaping compared to PS and can reduce unnecessary radiation exposure to surrounding non-cancerous cells. In addition, no physical scattering devices are needed as in PS, allowing more efficient proton delivery.

PBS is particularly advantageous for FLASH-RT. However, the present disclosure is not limited thereto, and PBS can be used with other radiotherapy techniques.

Similarly, techniques other than PBS can be used in FLASH-RT.

Radiation Optimization Techniques: SFUD and IMPT

The intensity of the charged particle beam is modulated individually so that a desired overall dose distribution of the charged particle beam in the target or target volume is achieved. When using pencil proton beams, two optimization methods can be considered, among others: Single Field Uniform Dose (SFUD) and Intensity Modulated Proton Therapy (IMPT).

In a SFUD process, each individual proton beam is optimized to achieve an essentially uniform dose for that specific proton beam across at least a portion of the target or target volume having a tumor therein. It is noted that often more than one proton beam is used for a more specific target irradiation. In this case, each proton beam of two or more proton beams is optimized to achieve an essentially homogeneous distribution.

Figure 3A:
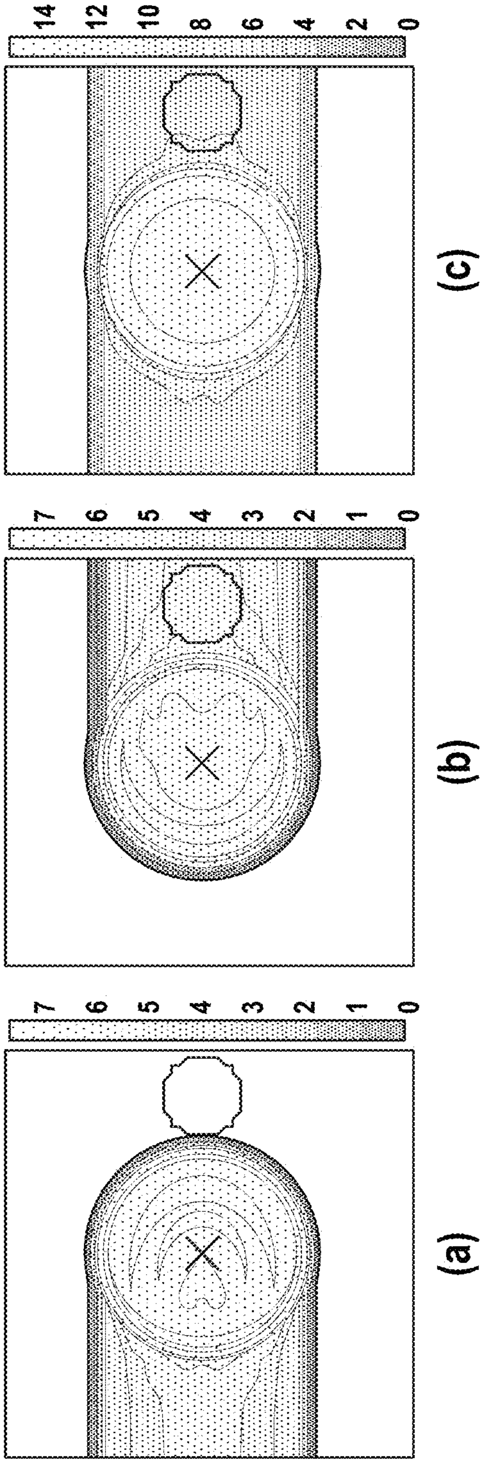
FIG. 3A shows a dose distribution for two SFUD proton beams covering a target volume.

For example, FIG. 3A shows a dose distribution for two proton beams covering a target volume (indicated by the bigger circle in the middle of each dose map). The smaller circle represents an OAR. FIG. 3A (a) shows a first proton beam (gantry angle of) 90° having an essentially uniform dose distribution, FIG. 3A (b) shows a second proton beam (gantry angle of) 270° having an essentially uniform dose distribution, and FIG. 3A (c) shows both proton beams covering the target volume to provide a total dose at the tumor location of, for example, 14 Gy.

In IMPT, each proton beam does not have to have a uniform dose distribution as in the SFUD approach. In other words, in IMPT, each proton beam can have a non-uniform dose distribution in at least a portion of the target or target volume. However, the weights of the individual proton beams can be optimized so that the overall dose distribution in at least a portion of the target or target volume is essentially uniform, regardless of the dose distributions of the individual proton beams.

Figure 3B:
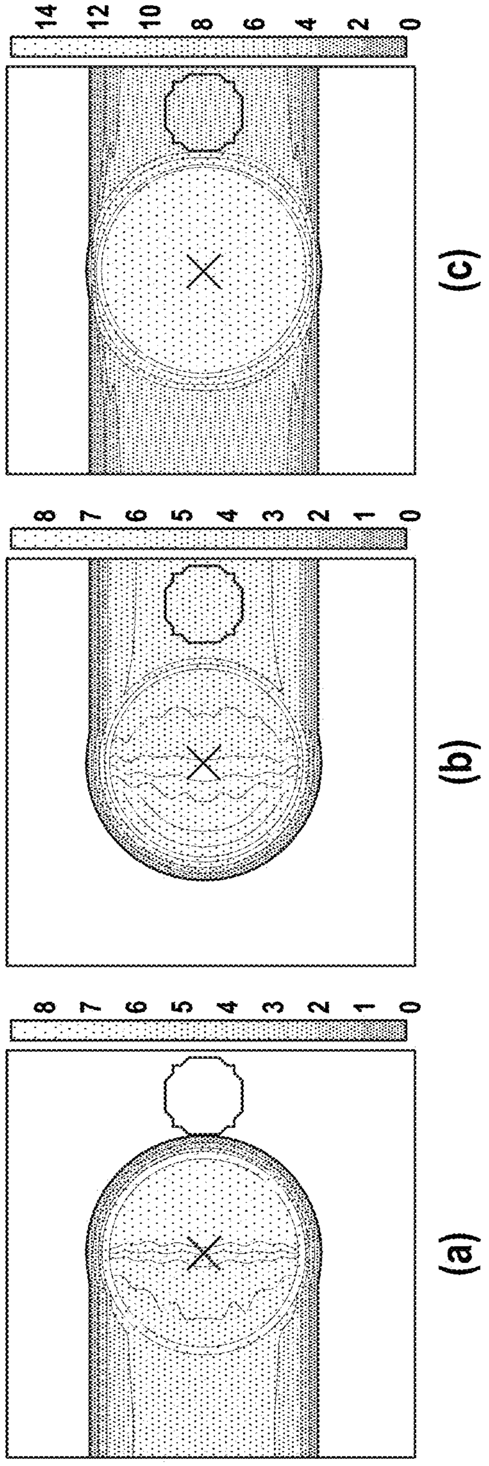
FIG. 3B shows a dose distribution for two IMPT proton beams covering a target volume.

FIG. 3B shows a dose distribution for two intensity-modulated proton beams covering a target volume (indicated by the bigger circle in the middle of each dose map). The smaller circle represents an OAR. FIG. 3B (a) shows a first proton beam (gantry angle of 90°) having a non-uniform or modulated dose distribution, FIG. 3B (b) shows a second proton beam (gantry angle of 270°) having a non-uniform or modulated dose distribution, and FIG. 3A (c) shows both proton beams covering the target volume to provide a total dose at the tumor location of, for example, 14 Gy.

Compared to SFUD, IMPT allows for more flexible modulation of the beams as each pencil proton beam is individually optimized. As a result, IMPT allows greater sparing of critical structures that can be in the beam path, such as OARs, without significantly affecting the therapeutic dose at the tumor.

Multi-Beam FLASH Radiotherapy: Geometry

In multi-field IMPT, the creation of regions where different beams overlap is not a problem because a contribution from each beam is modulated so that the total dose deposited at the target is equal to the therapeutic dose. In FLASH radiotherapy, however, there is a minimum dose and dose rate that must be deposited in the critical healthy structures in order for them to be protected by the FLASH effect. Thus, if all beams penetrate a healthy structure, each beam will deposit at least the same minimum dose at the target.

Consequently, a larger overdose occurs in the area where the three beams overlap in the target.

Figure 4:
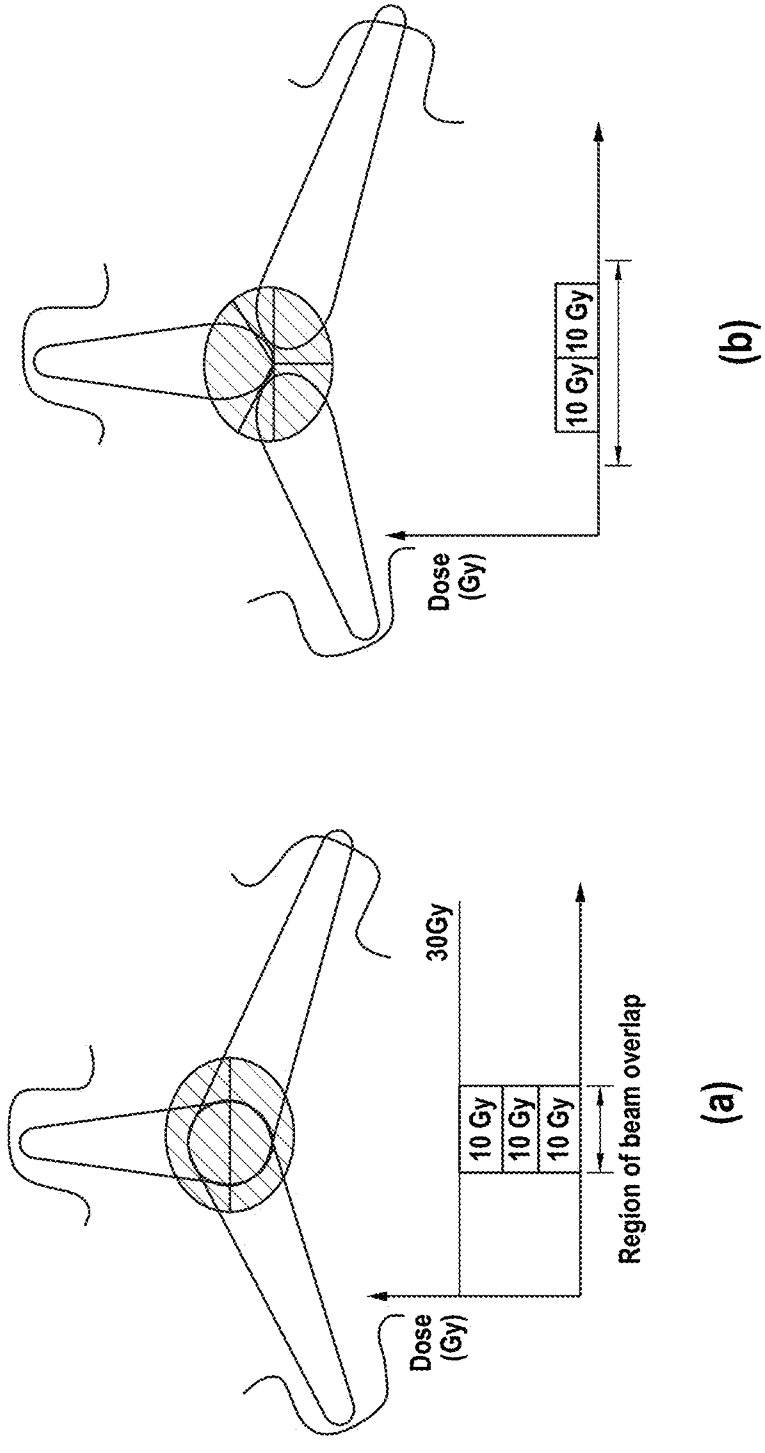
FIG. 4 shows a full IMPT irradiation of a target and an adapted batch-based irradiation of a target.

As shown in FIG. 4 (*a*), if 10 Gy is considered the minimum dose for the FLASH effect, the total dose is at least 30 Gy=3×10 Gy when the three beams are irradiated under FLASH conditions. This total dose exceeds the total dose that can be delivered to a tissue in a given irradiation fraction because it can cause large toxic effects. Therefore, this geometry must be modified to achieve the FLASH minimum dose while avoiding extreme toxicity effects to the patient.

One solution is an adapted patch-based geometry of the target region. In this case, each of the beams is responsible for irradiating a specific patch of the target, as illustrated in FIG. 4 (*b*). In an adapted patched-based geometry, each beam is also irradiated with 10 Gy per pulse, but the lack of an overlap area prevents the creation of overdose areas.

The beams for the adapted patch-based geometry can be generated using, for example, 3D range modulators such as the 3D range modulator described in Weber et al. (FLASH radiotherapy with carbon ion beams. *Med Phys*. 2021; 00:1-19. https://doi.org/10.1002/mp.15135).

However, in the adapted patch-based geometry, only a limited number of patches that match the total number of beams is created, avoiding the creation of matching lines in between patches. Therefore, the matched patch-based irradiation of the target would only provide partial coverage of the tumor, which also compromises effective control. To address this problem, the inventors have developed a novel geometry for irradiating the tumor. Hereinafter, this novel geometry will be referred to as the "stitching geometry."

Figure 5:
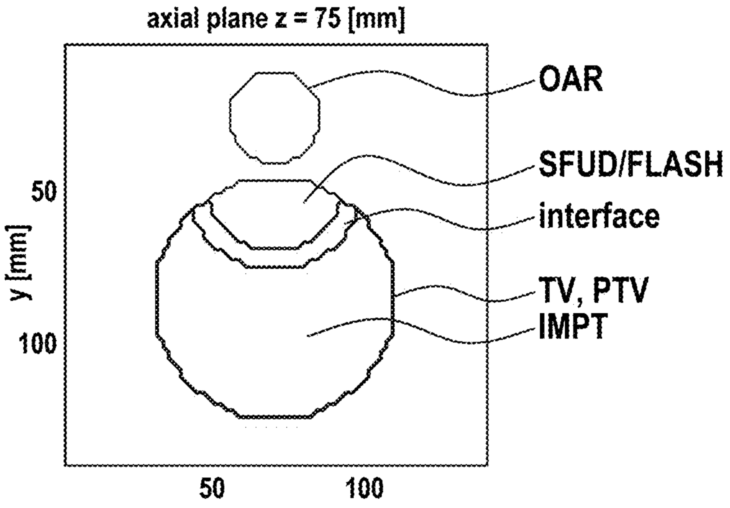
FIG. 5 shows a stitching geometry according to embodiments of the present disclosure.

FIG. 5 shows a stitching geometry according to embodiments of the present disclosure.

According to the embodiments of the present disclosure, the stitching geometry is obtained by: generating one or more ultra-high dose rate charged particle beams (e.g., SFUD FLASH proton beams) such that each ultra-high dose rate charged particle beam provides a substantially uniform first dose distribution in a corresponding first region of a target region; generating one or more intensity-modulated beams (e.g., IMPT beams) such that the one or more intensity-modulated beams provide a substantially uniform second dose distribution in a second region of the target region different from the first region; and irradiating the one or more ultra-high dose rate charged particle beams and one or more intensity-modulated beams such that a substantially uniform total dose distribution is provided across the first region and the second region.

Accordingly, the ultra-high dose rate charged particle beams can be modulated to achieve the FLASH effect at OARs while avoiding overdosing scenarios.

In some embodiments, the ultra-high dose rate charged particle beams can be scattered beams generated with ridge filters. Thus, when irradiating the tumor, each FLASH beam can be considered a scattered beam that irradiates a region of the tumor. FLASH beams must deposit a minimum dose and dose rate in the organs to be protected.

In addition to the initial FLASH irradiation of, for example, the adapted patch-geometry of FIG. 4 (*b*), one or more intensity-modulated beams are used to irradiate the remaining volume of the target region. For this purpose, an optimized stitching geometry is used to merge the different irradiated regions. In particular, the one or more intensity-modulated beams contribute to the complete homogeneous coverage of the target and prevent the formation of cold spots, i.e., the one or more intensity-modulated beams "stitch" the FLASH regions.

In the exemplary stitching geometry of FIG. 5 a single OAR is considered, and thus a single SFUD/FLASH region. The target region TV (e.g., the PTV shown in FIG. 2) is segmented in the single SFUD/FLASH region, interface region, and IMPT region.

In detail, the SFUD/FLASH region is first covered with a uniform dose distribution. A beam direction can be in the direction of the OAR, which is close to the target and must be spared. Since the uniform dose distribution can be modeled based on a distal edge of the target, the shape of the SFUD/FLASH region is idealized as a "projection" of the OAR toward the target. This facilitates complete coverage of the OAR with the FLASH beam while avoiding the appearance of edges on the beam that are more difficult to modulate.

The IMPT region is the volume of the target region TV which is only irradiated with the IMPT beams.

The interface region, located between the SFUD/FLASH region and the IMPT region, is the match-line between the two irradiations and can be susceptible to dose fluctuations. These fluctuations can be responsible for the development of hotspots in this region. Therefore, the dose irradiated in this region by the IMPT beams should be carefully evaluated.

In addition to the target, one or more (e.g., spherical) OARs can be positioned around the target. Since the OARs are to be spared by the FLASH effect, each FLASH beam penetrates a corresponding OAR. Consequently, the number of FLASH beams considered for a given treatment plan corresponds to the number of OARs positioned around the target. In the example shown in FIG. 5, only one OAR is positioned around the target, so only one FLASH beam is used in this treatment.

Figure 6:
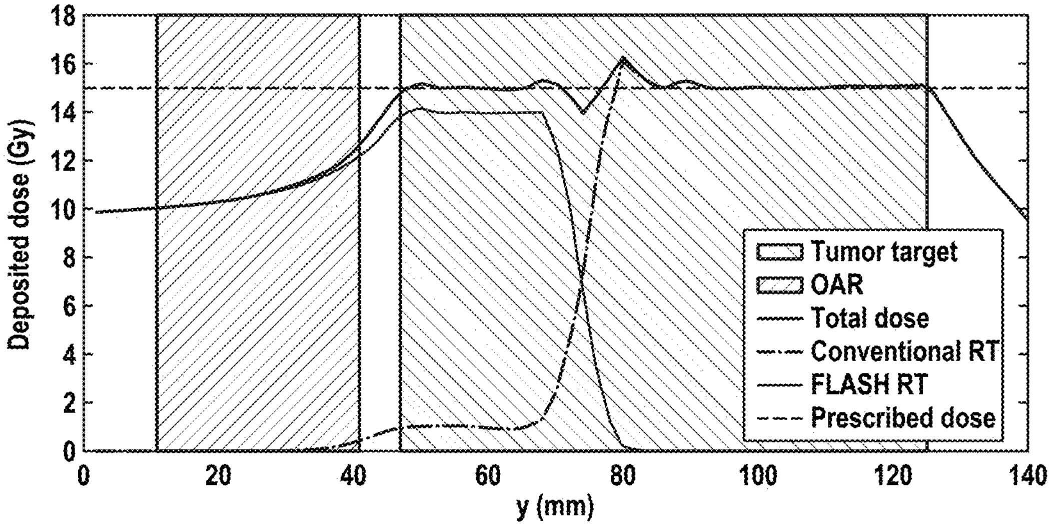
FIG. 6 shows a vertical dose profile for providing a stitching geometry according to embodiments of the present disclosure.

FIG. 6 shows a vertical dose profile for providing the stitching geometry of FIG. 5 according to embodiments of the present disclosure. In the example of FIG. 6, a FLASH minimum dose of 10 Gy was considered. The dashed horizontal line at 15 Gy represents a therapeutic dose prescription.

As can be seen, the FLASH radiation provides the FLASH minimum dose of 10 Gy at the OAR and a substantially uniform dose distribution in a first region of the target. The IMPT radiation does not contribute to the dose deposited at the OAR, but provides a substantially uniform dose distribution in a second region of the target that is different from the first region. In particular, the IMPT radiation locally "fills up" the dose previously provided by the FLASH radiation. In sum, the FLASH radiation and the IMPT radiation provide a substantially uniform total dose distribution in the target region.

Figure 7:
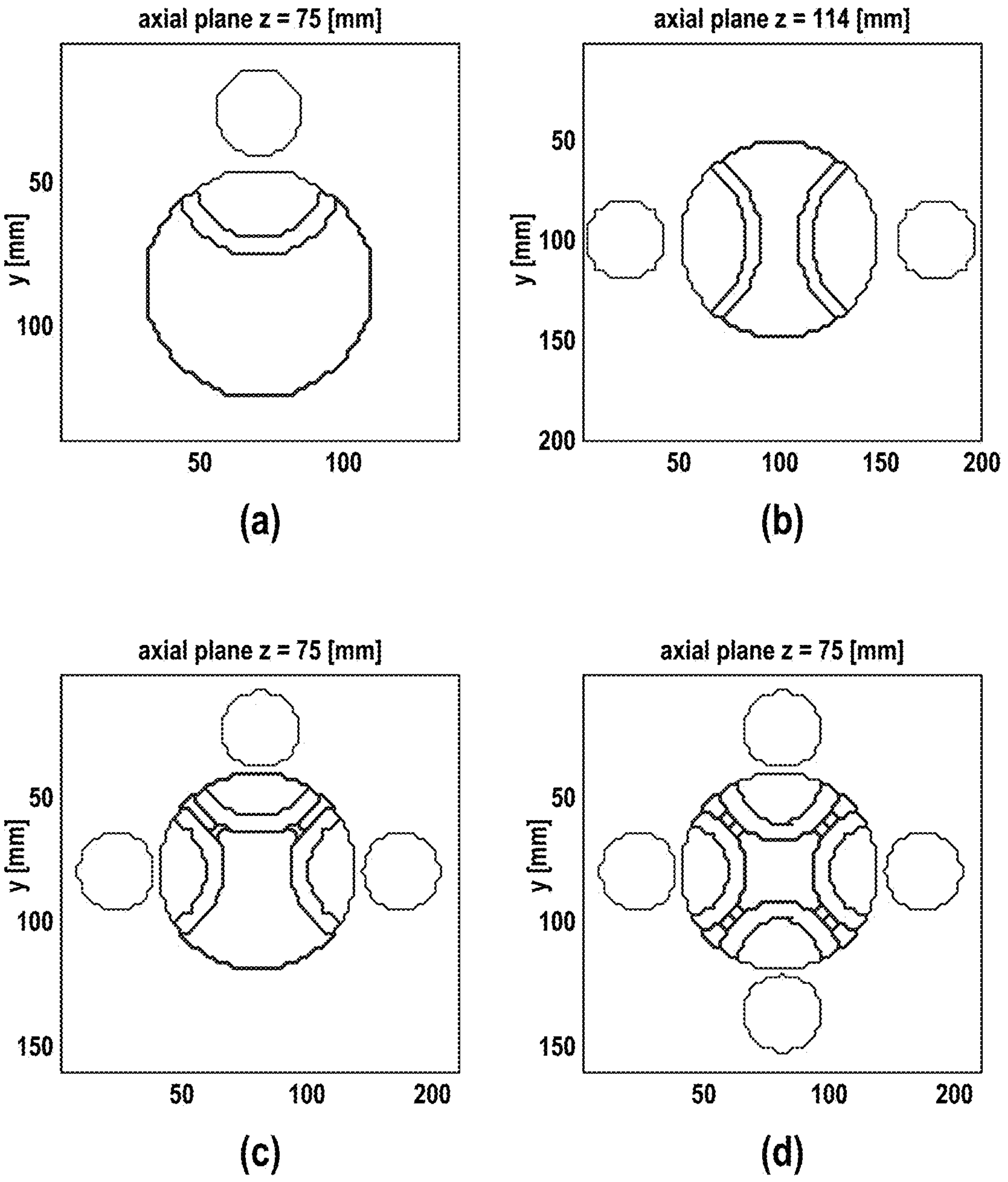
FIG. 7 shows various stitching geometries according to embodiments of the present disclosure.

FIG. 7 shows various stitching geometries according to embodiments of the present disclosure.

FIG. 7 (*a*) shows a stitching geometry with one OAR at the target and one corresponding FLASH beam. FIG. 7 (*b*) shows a stitching geometry with two OARs at the target and two corresponding FLASH beams. FIG. 7 (*c*) shows a stitching geometry with three OARs at the target and three corresponding FLASH beams. FIG. 7 (*d*) shows a stitching geometry with four OARs at the target and four corresponding FLASH beams.

In the figures, the central sphere is the target volume that is irradiated. The target volume is segmented into the different regions of the stitching geometry: the SFUD/FLASH region (in red), the interface region (in purple), and the IMPT region (in pink). In addition, the different spherical OARs are arranged in the same direction as the SFUD/FLASH regions (in yellow).

The exemplary stitching geometries of FIG. 7 were implemented on the matRad open-source dose calculation tool inside a box water phantom, considering a Computerized Tomography (CT) grid with [2 2 3] mm resolution in x, y and z directions respectively. All SFUD/FLASH beams were irradiated with a treatment couch angle of 0°, while only directly opposing directions were considered for the gantry angles. The four stitched-based geometries which were implemented on matRad and respective gantry angles are discriminated in FIG. 7.

Apparatus for Radiotherapy

Figure 8:
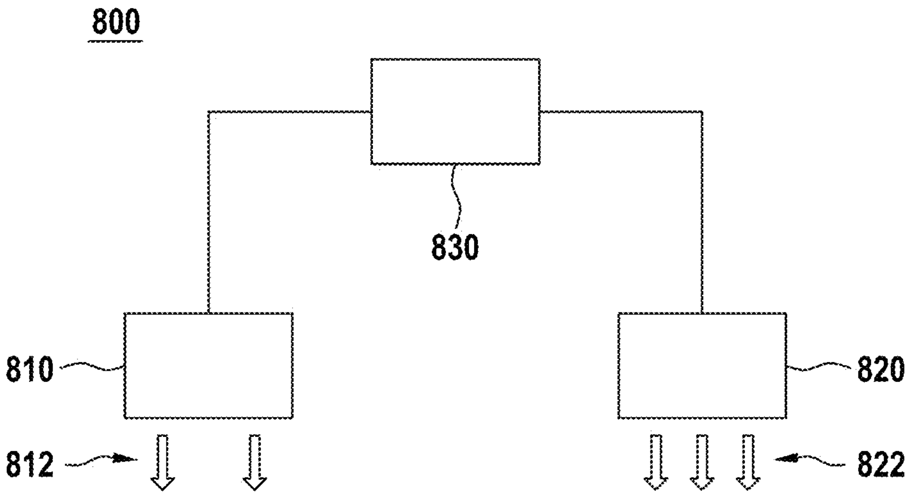
FIG. 8 shows an apparatus for radiotherapy according to embodiments of the present disclosure.
Figure 9:
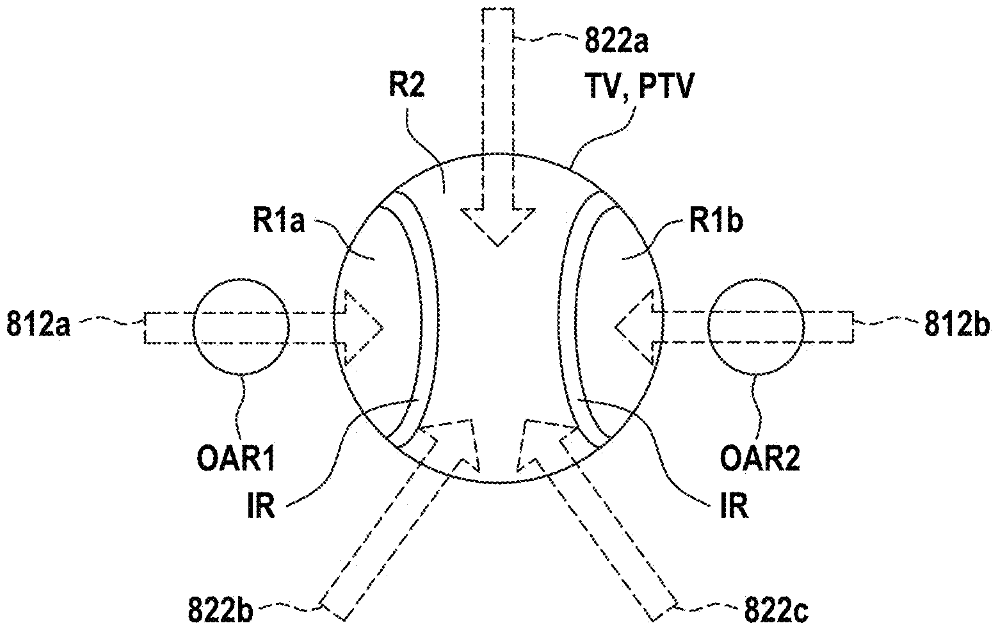
FIG. 9 shows a target volume irradiated using the apparatus for radiotherapy according to the embodiments of the present disclosure.

FIG. 8 shows an apparatus 800 for radiotherapy, in particular FLASH radiotherapy, according to embodiments of the present disclosure. FIG. 9 shows a target volume TV irradiated using the apparatus 800 for radiotherapy of FIG. 8.

The apparatus 800 includes at least one first radiation source 810 configured to provide or emit one or more ultra-high dose rate charged particle beams 812 and at least one second radiation source 820 configured to provide or emit one or more intensity-modulated beams 822.

The at least one first radiation source 810 is a charged particle source configured to emit the one or more ultra-high dose rate charged particle beams 812. The one or more ultra-high dose rate charged particle beams 812 can be Single Field Uniform Dose (SFUD) beams. In some embodiments, the charged particles are protons, ions, or electrons. In a preferred embodiment, the charged particles are protons.

The at least one second radiation source 820 is configured to provide the one or more intensity-modulated beams 822, which can be photon beams (e.g., X-ray), proton beams, electron beams, or ion beams. In a preferred embodiment, the one or more intensity-modulated beams 822 are proton beams. In particular, the one or more intensity-modulated beams 822 can be Intensity Modulated Proton Therapy (IMPT) beams.

The apparatus 800 further includes a controller 830 configured to control the at least one first radiation source 810 and the at least one second radiation source 820.

In FIG. 9, a target region TV (e.g., a Planning Target Volume, PTV) is schematically shown. The spherical shape of the target region TV is for simplification only, and the target region TV, especially the PTV, can have any other shape depending on the circumstances in radiotherapy.

By way of example, two volumes of interest are shown adjacent to, and spatially separate from, the target region TV. The two volumes of interest include a first Organ At Risk OAR1 and a second Organ At Risk OAR2. The spherical shape of the volumes of interest is for simplification only, and the volumes of interest, especially the Organs At Risk, can have any other shape depending on, for example, a patient's physiology. Furthermore, it is to be understood that one volume of interest or more than two volumes of interest can be present.

The controller 830 can be configured to control the at least one first radiation source 810 to generate the one or more ultra-high dose rate charged particle beams 812 such that each ultra-high dose rate charged particle beam of the one or more ultra-high dose rate charged particle beams 812 provides a substantially uniform first dose distribution in a corresponding first region of a target region TV (e.g., a Planning Target Volume, PTV).

In the example of FIG. 9, a first ultra-high dose rate charged particle beam 812*a* provides a substantially uniform first dose distribution in a corresponding first region R1*a* of the target region TV. A second ultra-high dose rate charged particle beam 812*a* provides a substantially uniform first dose distribution in another corresponding first region R1*b* of the target region TV.

If multiple ultra-high dose rate charged particle beams are used in the radiotherapy, a corresponding number of first regions can be defined. In other words, the number of ultra-high dose rate charged particle beams and the number of first regions can be the same. The first regions can be separate from each other, i.e., the first regions might not overlap.

The controller 830 can be configured to control the at least one first radiation source 810 such that each ultra-high dose rate charged particle beam passes through a respective volume of interest. In a preferred embodiment, the number of ultra-high dose rate charged particle beams, and thus the number of first regions, can be selected to correspond to the number of volumes of interest determined, for example, by medical personnel such as a physician or an algorithm.

In the example of FIG. 9, the first ultra-high dose rate charged particle beam 812*a* passes through the first Organ At Risk OAR1, and the second ultra-high dose rate charged particle beam 812*b* passes through the second Organ At Risk OAR2. Thereby, a protective effect, in particular the FLASH effect, can be achieved in the first Organ At Risk OAR1 and the Organ At Risk OAR2.

In particular, the one or more ultra-high dose rate charged particle beams 812 provide a dose high enough to minimize toxicity effects in one or more volumes of interest, such as Organs At Risk, during radiotherapy. In some embodiments, the one or more ultra-high dose rate charged particle beams 812 can provide a dose high enough to produce the FLASH effect in the one or more volumes of interest. Thus, in some embodiments, the one or more ultra-high dose rate charged particle beams 812 can also be referred to as "FLASH beams". Constraints for the FLASH effect can include a minimum dose of 10 Gy in the one or more volumes of interest and a minimum dose rate of 40 Gy/s in the one or more volumes of interest.

The controller 830 can be configured to control the at least one second radiation source 820 to generate the one or more intensity-modulated beams 822, e.g., IMPT beams, such that the one or more intensity-modulated beams 822 provide a substantially uniform second dose distribution in a second region R2 of the target region TV different from the first region(s).

Therefore, the one or more intensity-modulated beams 822 contribute to the complete homogeneous coverage of the target region TV and prevent the formation of cold spots. In particular, the one or more intensity-modulated beams 822 can "stitch" the first (e.g., FLASH) regions or "fill in" the region(s) of the target volume TV not covered by the ultra-high dose rate charged particle beam(s) (e.g., FLASH beams).

The interface region IR, located between the first region(s) and the second region, is the match-line between the two irradiations and can be susceptible to dose fluctuations. These fluctuations can be responsible for the development of hotspots in this region. Therefore, the dose irradiated in this region by the one or more intensity-modulated beams 822 should be carefully evaluated.

A number of the intensity-modulated beams 822 can be selected to provide a good, preferably full, coverage of the region(s) of the target volume TV not covered by the ultra-high dose rate charged particle beam(s). In the example of FIG. 9, three intensity-modulated beams 822*a*, 822*b* and 822*c* are shown. However, one, two, or more than three intensity-modulated beams can be used.

When multiple intensity-modulated beams are used, these beams can be adapted to jointly cover the entire second region R2. In particular, the second region R2 can have a plurality of sub-regions, wherein each intensity-modulated beam of the plurality of intensity-modulated beams is adapted to irradiate a respective sub-region. Accordingly, a number of sub-regions of the second region R2 can correspond to a number of intensity-modulated beams. Because the beams are intensity modulated, the sub-regions of the second region R2 can at least partially overlap such that the doses provided by the plurality of intensity-modulated beams add up to provide the substantially uniform second dose distribution across the entire second region R2.

Preferably, the controller 830 is further configured to control the at least one second radiation source 820 such that the one or more intensity-modulated beams 822 do not pass through a volume of interest. Thereby, volume of interest, such as OARs, can be protected.

In some embodiments, the one or more ultra-high dose rate charged particle beams 812 and the one or more intensity-modulated beams 822 are generated sequentially. For example, the one or more ultra-high dose rate charged particle beams 812 and the one or more intensity-modulated beams 822 can be pulsed beams that are generated and emitted intermittently.

According to some embodiments, which can be combined with other embodiments herein, the controller 830 is further configured to control the at least one first radiation source 810 and the at least one second radiation source 820 to provide a substantially uniform total dose distribution across the first region(s) and the second region. Accordingly, the same doses can be provided to the first region(s) and the second region.

Dose and Dose Rate Calculation

The one or more ultra-high dose rate charged particle beams and the one or more intensity-modulated beams are interdependent, i.e., the one or more ultra-high dose rate charged particle beams and the one or more intensity-modulated beams, in particular the doses and dose rates provided by them, cannot be considered independently from each other. Therefore, processes are needed to determine doses and does rates for a given target volume.

In the following, two exemplary processes for determining doses and does rates for a treatment are explained with respect to FIGS. 10 and 11. However, the present disclosure is not limited thereto, and other processes can be used which can provide the substantially uniform dose distribution in the target, such as a PTV.

Figure 10:
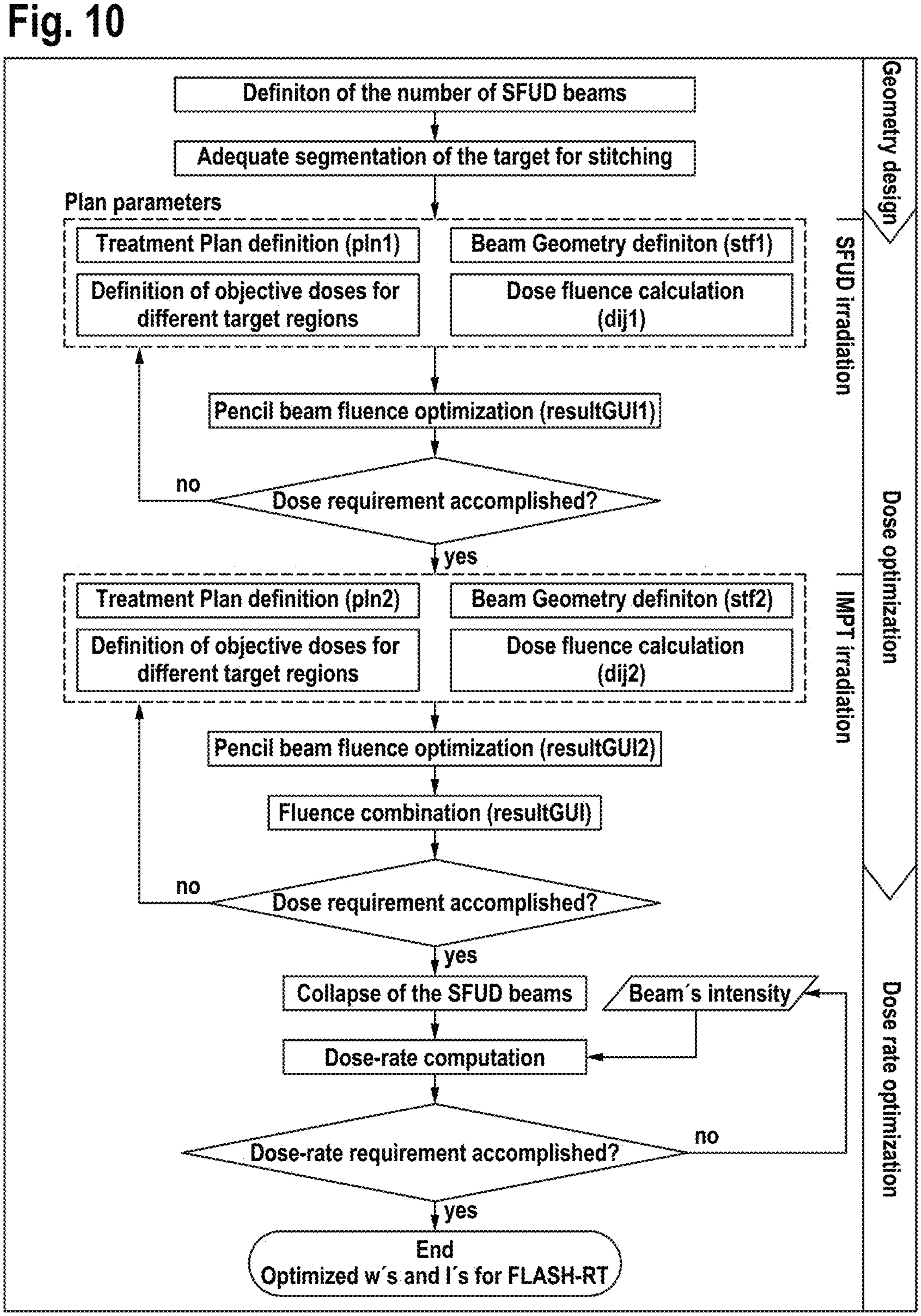
FIG. 10 shows a workflow of FLASH treatment planning when dose and dose rate are sequentially optimized.

FIG. 10 shows a workflow of a FLASH treatment planning when dose and dose rate are sequentially optimized.

First, the target volume is segmented for stitching. An example segmented target volume is shown in FIG. 2. Then, two steps are performed sequentially: dose optimization and dose rate optimization.

Dose Optimization

The fluence of the various FLASH beams is initially optimized based solely on the imposed dose constraints. Thus, the focus is on achieving the total therapeutic dose and verifying the minimum FLASH dose in the healthy structures to be protected (the OARs). In this optimization strategy, a dose target is not set a priori for the entire PTV. Instead, different dose targets are defined for each region of the stitching geometry during the development of the plan.

First, the dose deposited by the FLASH beams is investigated. In the exemplary stitching geometries, these beams always penetrate an OAR, which should be protected by the FLASH effect, before irradiating the target region. Consequently, the optimization of these beams focuses on achieving a minimum dose of, for example, 10 Gy in these regions to be protected. Each FLASH beam irradiates only a portion of the target, the FLASH region. Therefore, these are the only regions assigned a dose target for this radiation. This dose target assignment is determined on a trial-and-error basis until the resulting dose distribution meets the required minimum dose in the FLASH regions.

Successively, the dose delivered by the intensity-modulated beams is optimized with the aim of providing the dose that is missing for the total therapeutic prescription. Therefore, the dose originally delivered by the FLASH beams must be taken into account. The intensity-modulated beams irradiate each region of the PTV with more or less dose, depending on whether the region was previously irradiated by the FLASH beams or not. Consequently, a separate dose target must be defined for each irradiated region of the stitching geometry. In analogy to FLASH irradiation, the combination of different dose targets is tested until a conformal and homogeneous dose deposition is provided.

At the end of such a dose optimization, a set of optimal fluences and intensities can be determined for both the FLASH beams and intensity-modulated beams.

Dose Rate Optimization

The intensities of the FLASH beams are optimized with a focus on achieving the minimum FLASH dose rate in the OARs. This dose rate constraint only affects the FLASH beams, so the optimization of the intensity of these beams must be done more carefully.

Prior to optimizing the intensities of the FLASH beams, each FLASH beam can be collapsed into a single scattered pencil beam. Although this step does not introduce any changes in the dose deposition of the beam, considering a single energy scattered beam for FLASH irradiation also reduces the inherent variability associated with the dose-averaged dose rate.

Since each FLASH beam is a single pencil beam, the minimum intensity at which this beam must be irradiated for a minimum of 40 Gy/s to be deposited in the OAR can be calculated as follows:

$$I_{beam\ a} = \max\left(\frac{40}{d'_{ia}}\right)$$

where $I_{beam\ a}$ is the intensity calculated for beam a, $d'_{ia}$ is the influence matrix calculated after collapsing the same beam, and i considers the voxels in which OARs are defined.

If no constraints are set for the dose rate at which a particular beam must be irradiated, it is assumed that this beam is irradiated with a default intensity. Therefore, a constant value for the intensity of the intensity-modulated beam is automatically set. In one example, this value can be set to $2 \cdot 10^{10}$ protons/s, as this is the maximum beam intensity that can be generated in the facility of the Heidelberg Ion Beam Therapy Center (HIT).

Figure 11:
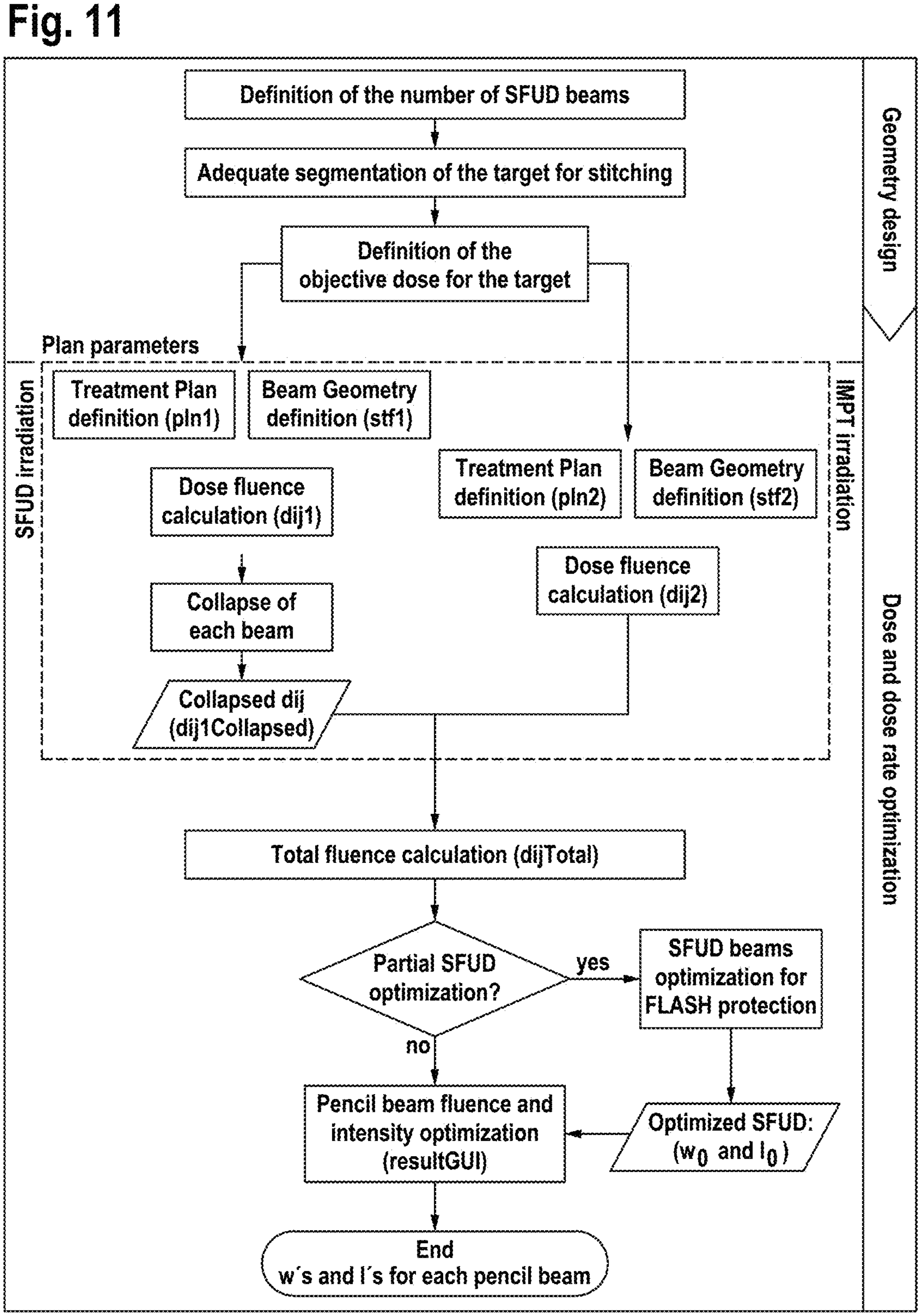
FIG. 11 shows a workflow of FLASH treatment planning when dose and dose rate are simultaneously optimized.

FIG. 11 shows a workflow of a FLASH treatment planning when dose and dose rate are simultaneously optimized.

First, the target volume is segmented for stitching. An example segmented target volume is shown in FIG. 2. Then, two steps are performed simultaneously: dose optimization and dose rate optimization.

Initially, the geometry of the FLASH beams and the intensity-modulated beams is generated as a function of the treatment plan parameters, and both dose influence matrices are calculated in parallel. The generated FLASH influence matrix is sequentially adjusted to a collapsed form to simulate a scattered beam.

Finally, both the collapsed FLASH influence matrix and the influence matrix generated for the intensity-modulated irradiation are combined into a total dij that is given as input to an optimizer. The generated influence matrix has a total of n+m columns, where the first n columns refer to the n FLASH beams included in the treatment and the following m columns refer to the total non-FLASH beams.

In this optimization strategy, only the therapeutic dose is defined as the target dose for the PTV, unlike sequential dose and dose rate optimization, where different regions have different target doses depending on the irradiation type. In sequence, the fluences and intensities of the beams are optimized with the goal of minimizing an objective function that takes into account both dose and dose rate constraints. Two examples of this simultaneous optimization strategy are as follows:

1. A partial optimization in which the FLASH beams and non-FLASH beams are optimized separately. In this implementation, the fluences and intensities of the FLASH beams are optimized first, focusing on achieving a minimum dose and an average dose rate of 10 Gy and 40 Gy/s in the OAR, respectively. Once this first optimization step is completed, the variables just optimized are used as input for the optimization of the intensity-modulated beams. In this way, the dose already deposited after FLASH irradiation is also taken into account in the fluence optimization of the intensity-modulated beams, avoiding overdose scenarios.

2. A total pencil beam optimization in which both the FLASH fluences and intensities and the fluences and intensities of the intensity-modulated beams are optimized simultaneously. This represents a more automated optimization approach, where both the necessary FLASH conditions and the total treatment prescription are optimized within the same cycle.

Figure 12:
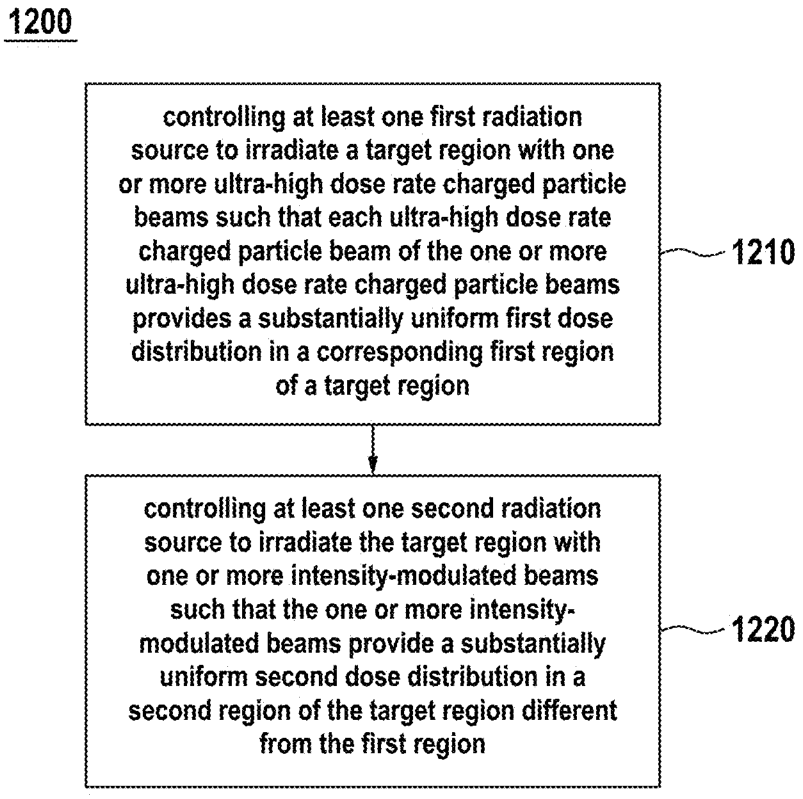
FIG. 12 shows a flowchart of a method of operating an apparatus for radiotherapy according to the embodiments of the present disclosure.

FIG. 12 shows a flowchart of a method 1200 of operating an apparatus for radiotherapy according to the embodiments of the present disclosure. The apparatus can be the apparatus described with respect to FIGS. 8 and 9.

The method 1200 includes in block 1210 controlling at least one first radiation source to irradiate a target region with one or more ultra-high dose rate charged particle beams such that each ultra-high dose rate charged particle beam of the one or more ultra-high dose rate charged particle beams provides a substantially uniform first dose distribution in a corresponding first region of a target region; and in block 1220 controlling at least one second radiation source to irradiate the target region with one or more intensity-modulated beams such that the one or more intensity-modulated beams provide a substantially uniform second dose distribution in a second region of the target region different from the first region.

The one or more intensity-modulated beams fill in doses of regions of the target volume not (fully) covered by the one or more ultra-high dose rate charged particle beams to provide a substantially uniform total dose distribution across the target region.

In some embodiments, the method 1200 further includes sequentially determining a dose and a dose rate for the target volume by: determining a configuration (e.g., fluence and/or intensity) of the one or more ultra-high dose rate charged particle beams based on one or more dose constraints; determining a configuration (e.g., fluence and/or intensity) of the one or more intensity-modulated beams based on a dose deposited in the target volume by the one or more ultra-high dose rate charged particle beams; and optimizing the configuration (e.g., fluence and/or intensity) of the one or more ultra-high dose rate charged particle beams based on one or more dose rate constraints.

In further embodiments, the method 1200 further includes simultaneously determining a dose and a dose rate for the target volume by: determining a first influence matrix for the one or more ultra-high dose rate charged particle beams and a second influence matrix for the one or more intensity-modulated beams; combining the first influence matrix and the second first influence matrix to obtain a combined matrix; and optimizing the combined matrix to determine a configuration (e.g., fluence and/or intensity) of the one or more ultra-high dose rate charged particle beams and a configuration (e.g., fluence and/or intensity) of the one or more intensity-modulated beams. The optimizing can be performed considering one or more dose constraints and one or more dose rate constraints at one or more volumes of interest (e.g., OARs).

The one or more dose constraints can include one or more FLASH constraints, such as a minimum dose to be deposited in one or more volumes of interest (e.g., OARs). For example, the minimum dose can be 8 Gy, 10 Gy or 12 Gy. Additionally, or alternatively, the one or more dose rate constraints can include one or more FLASH dose rate constraints, such as a minimum dose rate to be provided in one or more volumes of interest (e.g., OARs). For example, the minimum dose can be 40 Gy/s.

According to embodiments described herein, the method of operating an apparatus for radiotherapy can be conducted by means of computer programs, software, computer software products and the interrelated controllers, which can have a CPU, a memory, a user interface, and input and output means being in communication with the corresponding components of the apparatus for radiotherapy.

Figure 13:
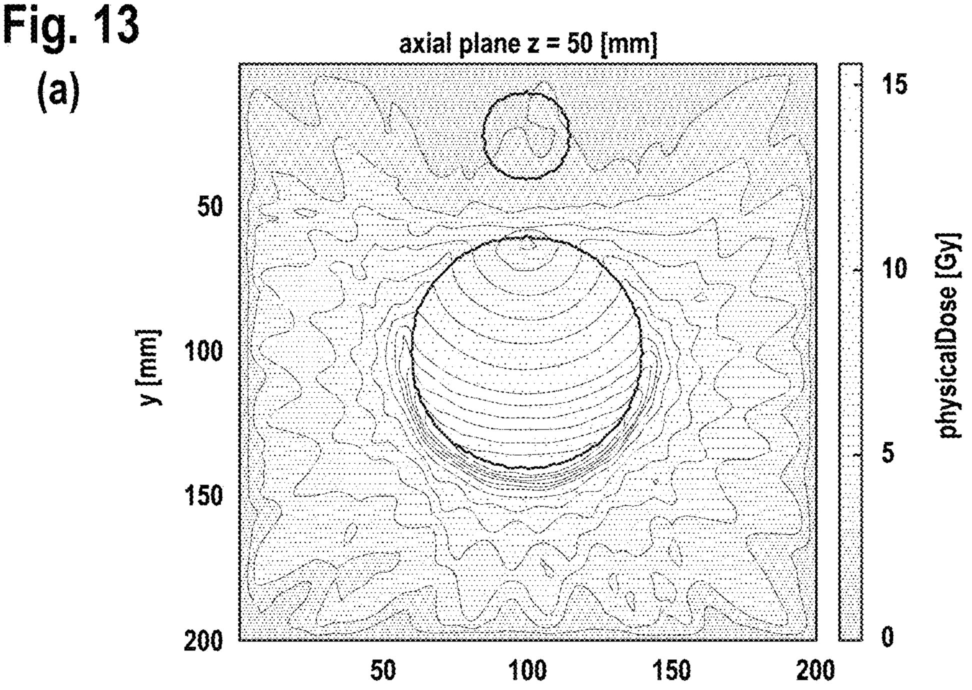
FIG. 13 shows dose distributions provided by an IMRT beam and a SFUD beam covering a target volume according to further embodiments of the present disclosure.
Figure 13:
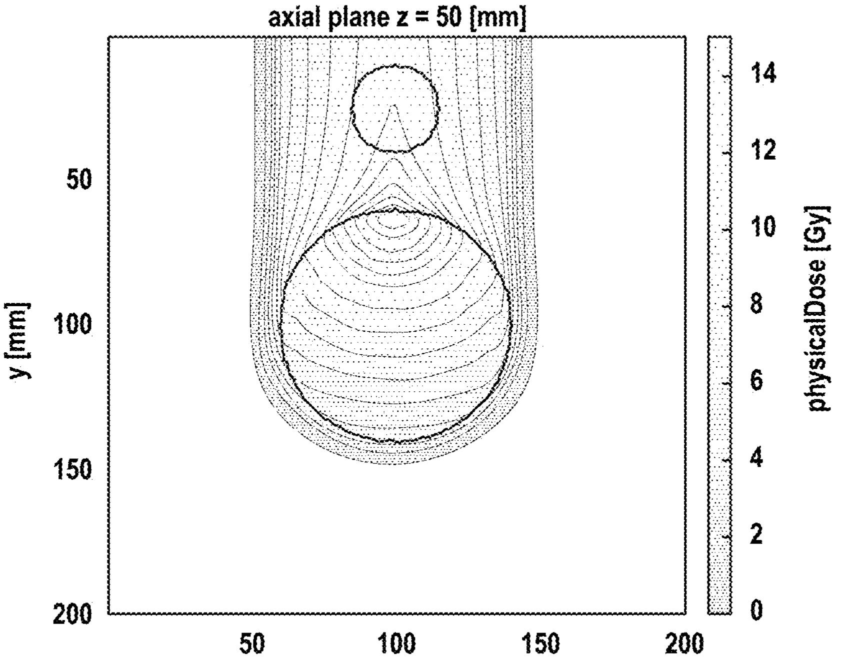
Figure 14:
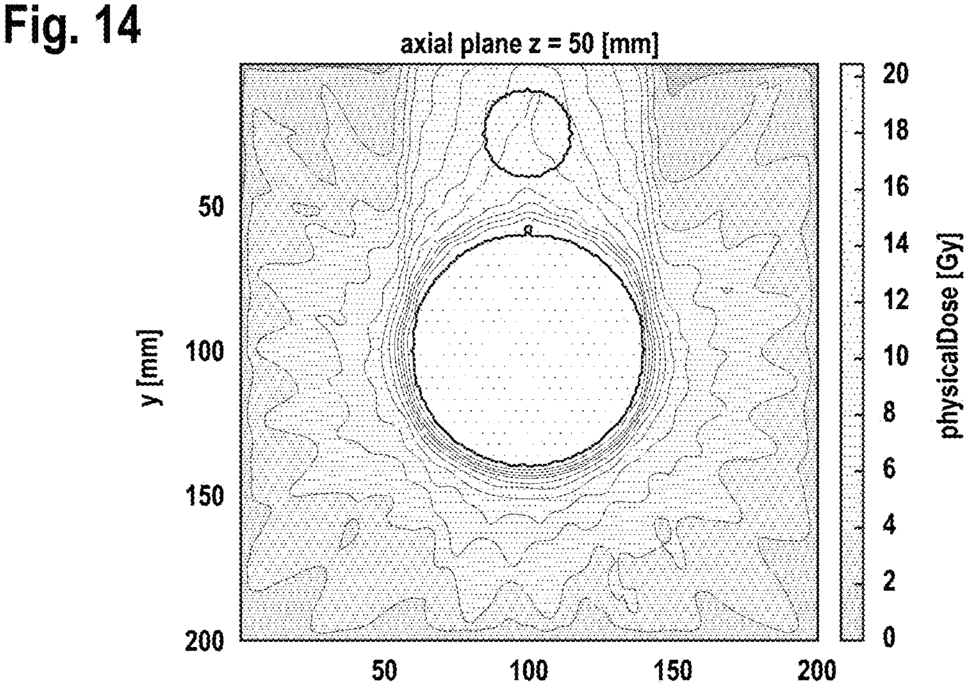
FIG. 14 shows a total dose of the IMRT beam and the SFUD beam of FIG. 13.
Figure 15:
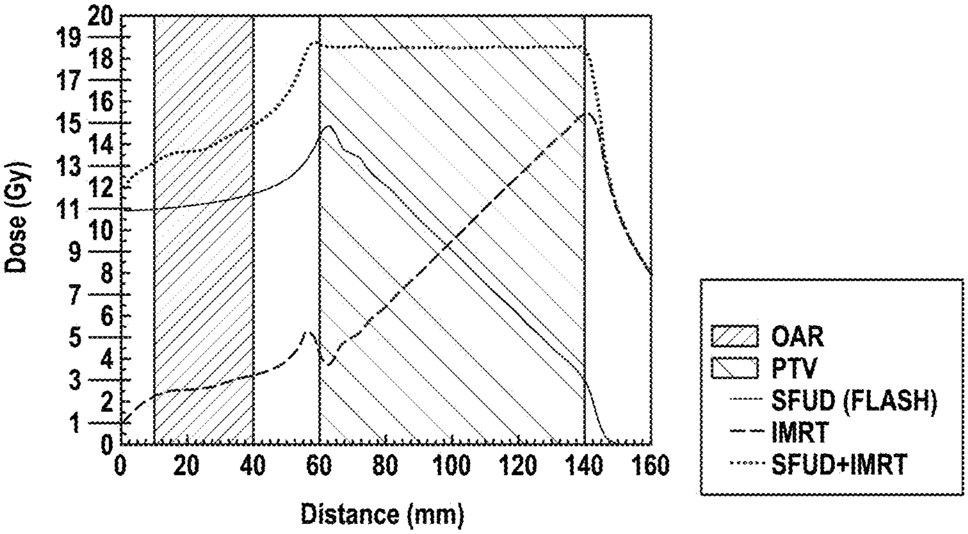
FIG. 15 shows a vertical dose profile of the IMRT beam and the SFUD beam of FIG. 13.

FIG. 13 shows dose distributions provided by an IMRT beam and a SFUD beam covering a target volume according to further embodiments of the present disclosure. FIG. 14 shows a total dose of the IMRT beam and the SFUD beam of FIG. 13. FIG. 15 shows a vertical dose profile of the IMRT beam and the SFUD beam of FIG. 13.

In the example of FIGS. 13 to 15, the dose distributions of the one or more ultra-high dose rate charged particle beams (IMRT; FIG. 13(*a*)) and the one or more intensity-modulated beams (SFUD; FIG. 13(*b*)) spatially overlap and add up in the target region to provide a substantially uniform total dose distribution across the target region.

In particular, the dose distribution of the one or more ultra-high dose rate charged particle beams across the target region is non-uniform, and the dose distribution of the one or more intensity-modulated beams across the target region is non-uniform to provide in sum the substantially uniform total dose distribution across the target region.

For example, as it is shown in FIG. 15, vertical dose profiles of the one or more ultra-high dose rate charged particle beams and the one or more intensity-modulated beams in the at least one interface region can each have a gradient to provide the non-uniform dose distributions across the target region. In some embodiments, the vertical dose profiles have opposite slopes, such as inclining and declining, respectively.

Therefore, the one or more ultra-high dose rate charged particle beams and the one or more intensity-modulated beams contribute to the complete homogeneous coverage of the target region and prevent the formation of cold spots. Furthermore, since the beams have non-uniform dose distributions across the target region, i.e., a wide range, the irradiation is robust against movement of the target. In particular, movement of the target within a considerable range does not affect the uniformity of the total dose distribution across the target region.

While the foregoing is directed to embodiments of the disclosure, other and further embodiments of the disclosure can be devised without departing from the basic scope thereof, and the scope thereof is determined by the claims that follow.

The invention claimed is:

1. An apparatus for radiotherapy, comprising:

at least one first radiation source configured to provide one or more ultra-high dose rate charged particle beams;

at least one second radiation source configured to provide one or more intensity-modulated beams; and a controller configured to:

control the at least one first radiation source to generate the one or more ultra-high dose rate charged particle beams and control the at least one second radiation source to generate the one or more intensity-modulated beams such that the one or more ultra-high dose rate charged particle beams and the one or more intensity-modulated beams provide a substantially uniform total dose distribution across the target region, wherein the controller is further configured to control the at least one first radiation source to generate the one or more ultra-high dose rate charged particle beams and control the at least one second radiation source to generate the one or more intensity-modulated beams such that a first dose distribution of the one or more ultra-high dose rate charged particle beams and a second dose distribution of the one or more intensity-modulated beams combine in the target region to provide the substantially uniform total dose distribution across the target region, in particular across substantially the entire target region.

2. The apparatus of claim 1, wherein the controller is further configured to:

control the at least one first radiation source to generate the one or more ultra-high dose rate charged particle beams such that each ultra-high dose rate charged particle beam of the one or more ultra-high dose rate charged particle beams provides a substantially uniform first dose distribution in a corresponding first region of the target region; and control the at least one second radiation source to generate the one or more intensity-modulated beams such that the one or more intensity-modulated beams provide a substantially uniform second dose distribution in a second region of the target region different from the first region.

3. The apparatus of claim 2, wherein the first region and the second region do not overlap.

4. The apparatus of claim 2, wherein the target region includes the first region, the second region and at least one interface region between the first region and the second region, in particular wherein the controller is further configured to control the at least one first radiation source to generate the one or more ultra-high dose rate charged particle beams and control the at least one second radiation source to generate the one or more intensity-modulated beams such that dose distributions of the one or more ultra-high dose rate charged particle beams and the one or more intensity-modulated beams spatially overlap and add up in the at least one interface region to provide the substantially uniform total dose distribution across the at least one interface region.

5. The apparatus of claim 1, wherein the controller is further configured to control the at least one first radiation source to generate the one or more ultra-high dose rate charged particle beams and control the at least one second radiation source to generate the one or more intensity-modulated beams such that dose distributions of the one or more ultra-high dose rate charged particle beams and the one or more intensity-modulated beams spatially overlap and add up in the target region to provide the substantially uniform total dose distribution across the target region.

6. The apparatus of claim 5, wherein the controller is further configured to:

control the at least one first radiation source to generate the one or more ultra-high dose rate charged particle beams such that the dose distribution of the one or more ultra-high dose rate charged particle beams across the target region is non-uniform; and control the at least one second radiation source to generate the one or more intensity-modulated beams such that the dose distribution of the one or more intensity-modulated beams across the target region is non-uniform, wherein the non-uniform dose distributions of the one or more ultra-high dose rate charged particle beams and the one or more intensity-modulated beams add up in the target region to provide the substantially uniform total dose distribution across the target region.

7. The apparatus of claim 1, wherein:

the one or more ultra-high dose rate charged particle beams are one or more FLASH beams; and/or the one or more ultra-high dose rate charged particle beams are one or more Single Field Uniform Dose, SFUD, beams; and/or the one or more ultra-high dose rate charged particle beams are modulated to provide a minimum dose of 8, 10 or 12 Gy in one or more volumes of interest and a minimum dose rate of 30, 40 or 50 Gy/s in the one or more volumes of interest, in particular wherein the one or more volumes of interest are spatially separated from the target region.

8. The apparatus of claim 7, wherein the one or more ultra-high dose rate charged particle beams are selected from the group consisting of proton beams, electron beams and ion beams.

9. The apparatus of claim 6, wherein the one or more intensity-modulated beams are selected from the group consisting of photon beams, proton beams, electron beams and ion beams.

10. The apparatus of claim 9, wherein the one or more intensity-modulated beams are Intensity Modulated Proton Therapy (IMPT), beams.

11. The apparatus of claim 10, wherein the one or more ultra-high dose rate charged particle beams and the one or more intensity-modulated beams are pulsed beams that are generated and provided to the target region intermittently.

12. The apparatus of claim 1, wherein the controller is configured to:

control the at least one first radiation source such that each ultra-high dose rate charged particle beam passes through a respective volume of interest; and/or control the at least one second radiation source such that the one or more intensity-modulated beams do not pass through a volume of interest.

13. A machine-readable storage medium having computer-executable instructions stored, that, when executed, cause one or more processors to perform:

control of at least one first radiation source to irradiate a target region with one or more ultra-high dose rate charged particle beams; and control of at least one second radiation source to irradiate the target region with one or more intensity-modulated beams, wherein control of the at least one first radiation source and the at least one second radiation source is performed such that the one or more ultra-high dose rate charged particle beams and the one or more intensity-modulated beams provide a substantially uniform total dose distribution across the target region, and a controller is further configured to control the at least one first radiation source to generate the one or more ultra-high dose rate charged particle beams and control the at least one second radiation source to generate the one or more intensity-modulated beams such that a first dose distribution of the one or more ultra-high dose rate charged particle beams and a second dose distribution of the one or more intensity-modulated beams combine in the target region to provide the substantially uniform total dose distribution across the target region, in particular across substantially the entire target region.

14. The machine-readable storage medium of claim 13 and having computer-executable instructions stored, that, when executed, cause the one or more processors to perform the functionalities of the apparatus according to claim 1.

* * * * *